United States Patent [19]

Conn

[11] 4,244,224
[45] Jan. 13, 1981

[54] AUTOMATIC SAMPLER FOR GAS AND LIQUID

[76] Inventor: Alvie P. Conn, 7926 Ridgeview, Houston, Tex. 77055

[21] Appl. No.: 31,067

[22] Filed: Apr. 18, 1979

[51] Int. Cl.³ .............................................. G01N 1/14
[52] U.S. Cl. .............................................. 73/422 TC
[58] Field of Search ............ 73/425.6, 422 TC, 421 B

[56] References Cited

U.S. PATENT DOCUMENTS

| | | | |
|---|---|---|---|
| 2,277,714 | 3/1942 | Polston et al. | 73/422 TC |
| 2,994,224 | 8/1961 | Brown | 73/421 B |
| 3,504,549 | 4/1970 | Davis et al. | 73/422 TC |

OTHER PUBLICATIONS

Tejas Gas Sampling System–A sales brochure of Tejas Instrument Engineers, 130 Lane Lane, Spring, TX 77373.
U.G.C. Electronic Sampler, A sales brochure of U.G.C. Industries Inc., P.O. Box 3736, Shreveport, LA 71103.
ARCO–Anubis Continuous Gas Sampler, Installation & Instructions, Bulletin No. 116-R2, Arcco Instrument Co., 7144 E. Condor St., Los Angeles, CA 90022.
Inline Relief & Sampler Head Assemblie, specifications & installation instructions, Welker Engineering Co., P.O. Box 1228, Bellaire, TX 77401.
Precision Valves, A specification brochure by Circle Seal Corporation, P.O. Box 3666, Anaheim, CA 92803. Circle Seal Controls Check Valves, General Applications CSP-23-L.5M.2/78.

*Primary Examiner*—S. Clement Swisher
*Attorney, Agent, or Firm*—Fulbright & Jaworski

[57] ABSTRACT

An automatic sampler for gases and liquids. The sampler has a pump which pumps a sample of a gas or a liquid from a source into a sample cylinder and a control mechanism for the pump. The control mechanism has a pressure regulator, an adjustable pneumatic timer, and a three-way button valve. The pump itself has an inlet valve which permits gas or liquid to flow into a cylinder. A piston in the cylinder moves to an appropriate position so that a desired size sample is trapped in the cylinder. The sample is then expelled through an outlet valve to a container such as a sample cylinder. The piston of the pump cylinder has a stinger projecting from one of its ends so that as the piston begins to move, the stinger shuts off the chamber that holds the sample. The inlet valve of the pump has a spring loaded plunger mounted within a cavity within the valve such that the plunger occupies a large part of the space in the cavity.

7 Claims, 2 Drawing Figures

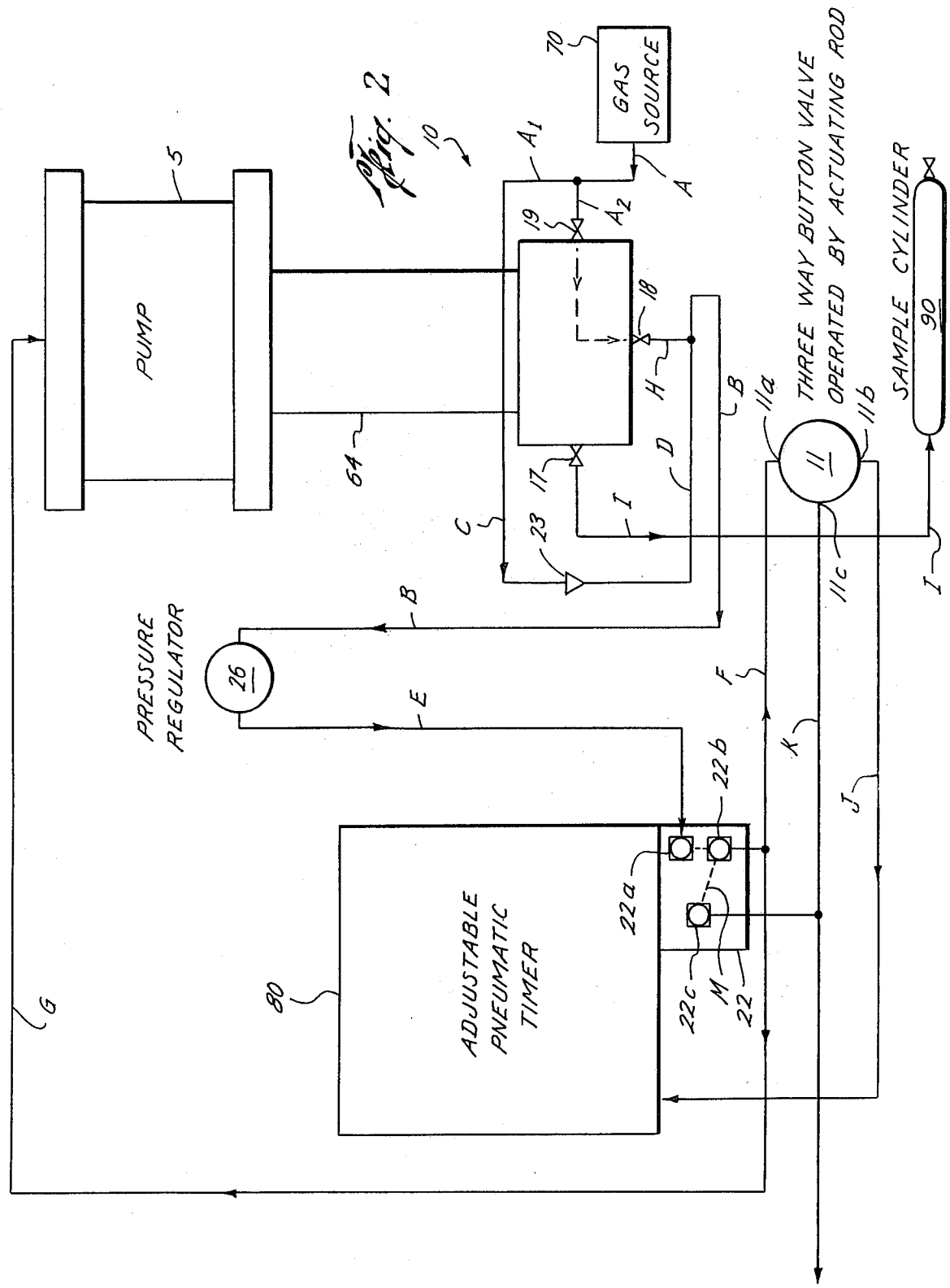

AUTOMATIC SAMPLER FOR GAS AND LIQUID

BACKGROUND OF THE INVENTION

1. Field of the Invention

The present invention relates to the field of automatic samplers for fluids such as gases and liquids. Such samplers are used, for example, to sample the gas flowing in a natural gas pipeline.

2. Description of the Prior Art

A variety of prior art samplers are of the "clock-wound regulator" type. These devices have a regulator that has an adjusting screw to adjust the discharge pressure of the gas flowing through the device. A clock is mechanically connected to the adjusting screw and as the clock turns, the adjusting screw turns also; but as the adjusting screw is turned down more and more torque is required to turn it due to the build-up of pressure in the sample container. Often during the day, a rise in temperature brings about an increase in pressure of the gas collected in the sample container or cylinder and this pressure reaches the demand pressure of the regulator so that no gas will enter the sample cylinder until the sample cylinder cools off enough for the contained pressure to drop below the demand pressure of the regulator, then more gas will flow into the sample cylinder. This causes erratic sampling between night and day.

In other prior art devices, a deformable cup at the bottom of a cylinder is contacted by a piston that pushes down on the cup. The gas or fluid contained in the cup is forced through a bore running through the piston as the piston pushes against and deforms the cup. Samplers of this type produce a sample of inaccurate size and they require considerable maintenance.

SUMMARY OF THE PRESENT INVENTION

The present invention discloses an automatic sampler for gas or liquid. The sampler has a pump that has an inlet valve, a pump cylinder, a pump cylinder piston, and an outlet valve. A controlling mechanism that includes a regulator, a pneumatic timer, and a three-way valve controls the flow of the gas or fluid through the inlet valve of the pump to the pump cylinder and through the pump outlet valve.

The inlet valve of the pump has a channel through which the gas or fluid to be sampled flows. A spring-loaded plunger is mounted in this channel which occupies a large part of the space in the channel so that when the inlet valve is closed, there is relatively little gas or fluid trapped in the channel. The gas flows through the inlet valve to the pump cylinder. A pump piston is mounted in the pump cylinder and the pump piston moves downward a desired distance so that a desired amount of gas or fluid is held within the pump cylinder. A purge valve is located at the bottom of the pump cylinder and as the pump piston moves downward in the pump cylinder, a stinger projecting from the pump piston enters and shuts off the purge valve so that the sample cannot escape from the pump cylinder. This purge valve automatically purges the pump cylinder each stroke. As the piston moves, pressure is built up in the pump cylinder and overcomes the spring tension in the outlet valve allowing gas to be discharged into the sample cylinder. The flow of the sample through the pump and the movement of the pump piston are controlled by a control system having a pneumatic timer, a pressure regulator, and a three-way valve. The timer controls the frequency at which sample aliquots are taken; for example, the timer can be set so that an aliquot of sample is taken once every ten minutes. The timer also actuates the pump piston to begin its downward movement in the pump cylinder.

The pressure regulator insures that only gas at a specified pressure will be applied to the pneumatic timer. For sampling gas, a relief valve is mounted between the pressure regulator and the pump. For sampling liquids, this relief valve is omitted.

The pneumatic timer has a three-way timer valve which is interconnected with both the pressure regulator and the three-way button valve for the control of the pump. A plurality of flow lines interconnect the various components of the sampler.

It is, therefore, an object of the present invention to provide an automatic sampler for gas or liquid.

Another object of the present invention is the provision of such a sampler that is pneumatic.

Yet another object of the present invention is the provision of such a sampler that requires no lubrication, that requires relatively little maintenance, that is efficient, and that does not require electricity for its operation.

Yet another object of the present is the provision of a sampler that can be used in remote areas where no conventional energy source such as electricity is available.

A further object of the present invention is the provision of a sampler which is compact and portable.

A still further object of the present invention is the provision of a sampler which is safe to operate.

An additional object of the present invention is the provision of a sampler which will pump a sample of substantially the same size for each sampling cycle over a prolonged period of time.

Another object of the present invention is the provision of a sampler which can operate at high pressures so that a sufficient sample can be taken which can be analyzed; for example, the burning of the sample in a calorimeter to determine the BTU content, analysis to determine the nitrogen and $CO_2$ content, the specific gravity, and the content of other components of interest.

A particular object of the present invention is the provision of a sampler having a pump having an inlet valve, the inlet valve having a spring-mounted plunger in a channel, the plunger of such a size that it occupies a large portion of the space in the channel. This valve could also consist of a ball and spring instead of plunger and spring.

Another particular object of the present invention is the provision of such a sampler in which a piston is mounted in the cylinder of the pump in which the sample is collected, the piston having projecting from one of its ends a stinger disposed so that the stinger enters a purge valve in one end of the cylinder when the piston begins to move in the cylinder.

Yet another particular object of the present invention is the provision of a sampler having a pump which is self-purging.

Still another particular object of the present invention is the provision of a sampler which can be used to sample either gas or liquid; when used to sample gas, the gas being sampled is used to operate the sampler and, when being used to sample liquid, a separate operating medium such as air or gas is used.

Another object of the present invention is the provision of a sampler which can be adjusted to take a sample of a desired size.

Other and further objects, features, and advantages of the present invention will be apparent from the following description of presently preferred embodiments thereof, taken in conjunction with the accompanying drawings.

BRIEF DESCRIPTION OF THE DRAWINGS

FIG. 2 is a schematic diagram of the sampler according to the present invention.

DESCRIPTION OF THE PREFERRED EMBODIMENT

Figure 1:
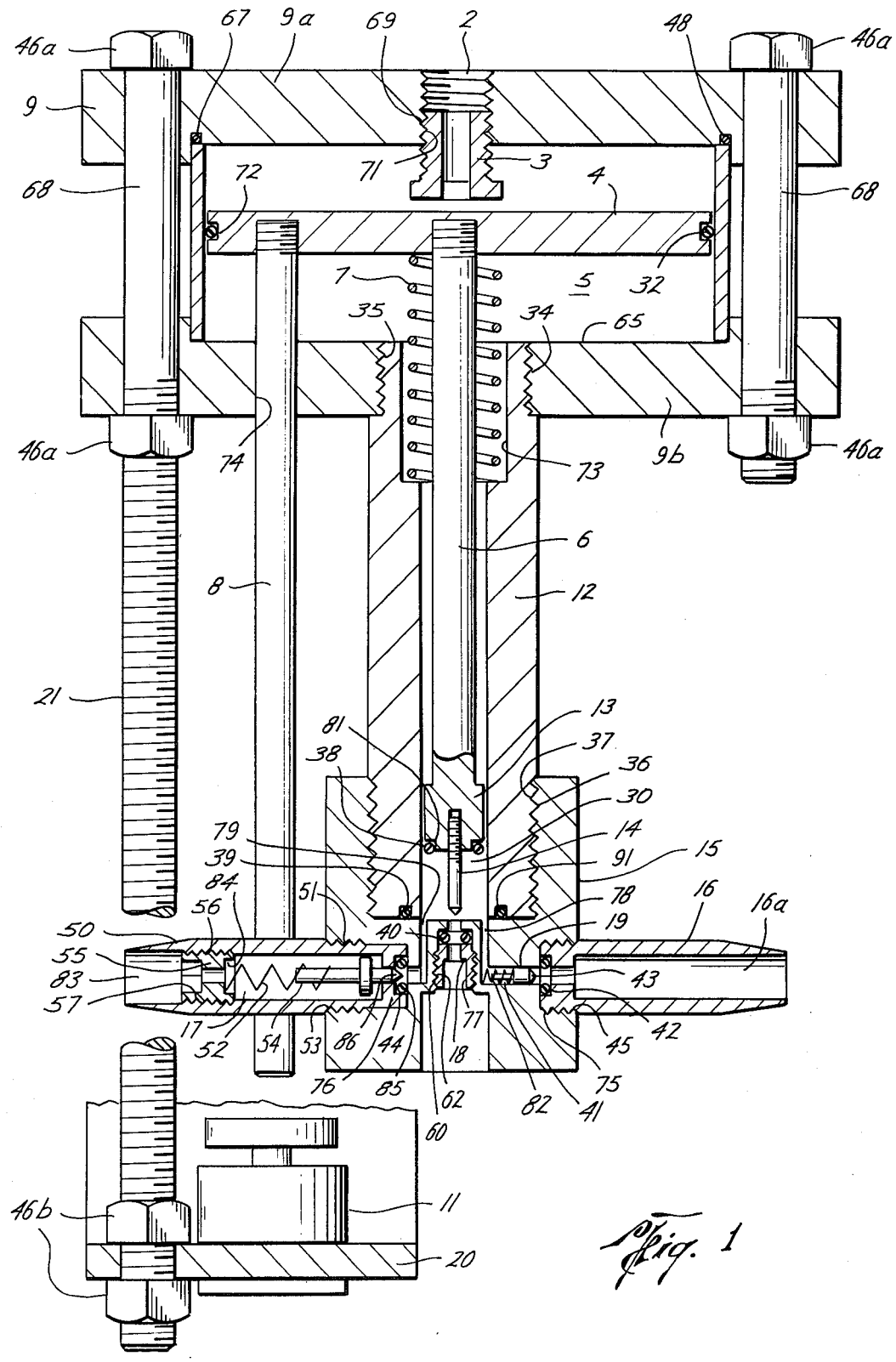
FIG. 1 is a side elevation view in cross section of the pump of the sampler according to the present invention.

As shown in FIG. 2, the sampler 10 according to the present invention has a pump 64, a regulator 26, a timer 80 with timer valve 22, and a three-way button valve 11. Gas for sampling is obtained from a gas source 70, for example, a natural gas pipeline, and after the sampler 10 has obtained the desired sample, the sample is introduced into sample cylinder 90 for storage. Although for purposes of disclosure the sampler 10 according to the present invention will be described with respect to the sampling of gas, it is to be understood that, with one minor modification, the sampler 10 according to the present invention may be used to sample liquids without departing from the spirit or scope of the invention. As shown in FIG. 2, the components of the sampler 10 are interconnected by a variety of lines A–M.

The pump 64 has a pump cylinder 12 having bore 30 extending longitudinally therethrough. The top of the pump cylinder 12 has the threads 35 formed integrally of its exterior for mating with the threads 34 of the bottom driver flange 9b for mounting the bottom driver flange 9b to the pump cylinder 12. The bottom driver flange 9b has the recess 65 for receiving the bottom of driver cylinder 5. The top driver flange 9a has a similar recess 66 for receiving the top of the driver cylinder 5. The O-ring 48 in the recess 67 of top driver flange 9a provides a seal between the top driver flange 9a and the driver cylinder 5. The driver cylinder 5 is held in position between the top driver flange 9a and the driver flange 9b, and the driver flange 9a is secured to the driver flange 9b by means of the driver tie bolts 68 and the nuts 46a. The tie bolt 21 acts to compensate for differences of expansion of the pump 64 and the mounting bracket 20 caused by temperature changes.

The top driver flange 9a is provided with the driver gas inlet 2 through which gas flows into the space enclosed by the driver cylinder 5. The driver gas inlet 2 has threads 69. The driver stroke adjuster 3 has threads 71 and is threadedly mounted in the driver gas inlet 2 and partially extends into the driver cylinder 5. The piston rod 6 extends from the driver cylinder 5 into the bore 30 of the pump cylinder 12. The piston rod 6 is secured to the driver piston 4 which is mounted in the driver cylinder 5. The driver piston 4 has recess 72 in which is mounted O-ring 32 to provide a seal between the driver piston 4 and the interior wall of the driver cylinder 5. The driver stroke adjuster 3 serves as a stop to prevent the driver piston 4 from proceeding further upward. By turning the driver stroke adjuster 3, the extent of travel of the driver piston 4 can be adjusted. The driver piston return spring 7 extends from the driver cylinder 5 into recess 73 of the pump cylinder 12.

The actuator rod 8 is secured to the driver piston 4 and extends from the driver piston 4 through the bore 74 in the bottom flange 9b so that when the driver piston 4 progresses downwardly, the actuator rod 8 contacts and actuates the button valve 11. The pump 64 is mounted to the mounting bracket 20 by means of the tie bolt 21, the bolts 68, the nuts 46a and the nuts 46b.

The pump cylinder head 15 is threadedly mounted to the bottom of the pump cylinder 12 by means of the threads 36 on the pump cylinder head 15 and the threads 37 on the pump cylinder 12. The O-ring 39 is placed in the recess 91 of the pump cylinder 12. The inlet tube 16 having the interior bore 16a is threadedly mounted in the opening 75 in the side of the pump cylinder head 15 by means of the threads 45 on the exterior of the inlet tube 16 and the threads 47 on the opening 75.

The outlet tube 50 is threadedly mounted in the opening 76 of the pump cylinder head 15 by means of the threads 53 on the exterior of the outlet tube 50 and the threads 51 on the wall of the opening 76.

The purge valve 18 is threadedly mounted in the opening 77 of the pump cylinder head 15 by means of the threads 60 on the exterior of the purge valve 18 and the thread 62 formed of the walls of the opening 77 of the pump cylinder head 15.

The right angle gas channel 78 extends from the bore 16a of the inlet tube 16 to the bore 30 of the pump cylinder 12. The inlet valve 19 is mounted within the right angle gas channel 78. The plunger 43 of the inlet valve 19 is movably mounted in the right angle gas channel 78 so that when the spring 41 pushes the plunger 43 outwardly, the plunger 43 comes in contact with the O-ring 42 thereby sealing shut the right angle gas channel 78.

The piston rod 6 has the pump piston 13 formed integrally of its bottom. The O-ring 38 is mounted in the recess 81 of the pump piston 13 to provide a seal between the pump piston 13 and the interior wall of the pump cylinder 12. The purge valve stinger 14 is secured to the pump piston 13 and disposed so that when the pump piston 13 moves downwardly, the purge valve stinger 14 enters the opening 77, contacts the O-ring 40 mounted in the recess 82 formed between the pump cylinder head 15 and the purge valve 18, and thereby shuts off the opening 77 from the bore 30 of the pump cylinder 12.

The discharge valve 17 is mounted in the bore 83 of the outlet tube 50. The valve body 55 of the discharge valve 17 is threadedly mounted to the interior of the outlet tube 50 by means of the threads 56 formed integrally of the exterior of the valve body 55 and the threads 57 formed on the interior of the bore 83 of the outlet tube 50. The spring 52 is mounted within the recess 84 of the valve body 55 and is also secured to the plunger 54 which is movably mounted within the bore 83. The plunger 54 is disposed so that when the spring 52 forces the plunger 54 inwardly, the plunger 54 contacts the O-ring 44 which is mounted in the recess 85 of the outlet tube 50 and the tip 86 of the plunger 54 seats in the right angle gas channel 79 in sealing contact thereby preventing communication between the right angle gas channel 79 and the bore 83 of the outlet tube 50.

When a cycle of the sampler 10 is initiated by the timer 80, gas flowing from the gas source 70 flows through lines A and A2 through the bore 16a of the inlet tube 16, through the inlet valve 19, through the right angle gas channel 78, into the bore 30 of the pump cylinder 12, through the opening 77 and the purge valve 18, then through lines H and B to the pressure regulator 26. Thus the pump cylinder 12 is purged each stroke. At the same time gas from the gas source 70 flows through lines A and A1 to line C and through line C to the relief valve 23. At this point in the cycle, the relief valve 23 prevents the gas flowing through line C to the top side of the relief valve 23 from flowing through the relief valve 23. At this same time, gas also flows through line H and line D to the bottom side of the relief valve 23.

After this initial flowing of gas from the gas source 70 to the pump 64 and the pressure regulator 26, the pressure inside the bore 30 of pump cylinder 12 equalizes with the pressure of the inlet gas from the gas source 70 allowing the spring 41 to push the plunger 43 outwardly thereby closing the inlet valve 19 and trapping a quantity of gas within the bore 30 of the pump cylinder 12.

Gas at reduced pressure flows from the regulator 26 through line E to the timer valve 22 of the timer 80. The gas enters port 22a of the timer valve 22, passes through line L to port 22b and then exits through line F to port 11a of the button valve 11. At this point, port 11a is closed and the gas is forced to flow back through line F to line G and through line G and the driver gas inlet 2 into the driver cylinder 5 thereby forcing the driver piston 4 downwardly. As the driver piston 4 moves downwardly, the piston rod 6 and the pump piston 13 also move downwardly.

As the pump piston 13 moves downwardly, the purge valve stinger 14 enters the O-ring 40 of the purge valve 18 thereby shutting off the gas through the line H causing a pressure drop in line D on the bottom side of the relief valve 23. At this point, the higher pressure in the line C forces the relief valve 23 to open allowing the high pressure gas in line C to flow through the relief valve 23, through the line D, through the line B, to the pressure regulator 26 thereby reestablishing high pressure gas up to the pressure regulator 26 and allowing the operating cycle to continue.

As the driver piston 4, the piston rod 6 and the pump piston 13 continue their downward stroke, pressure builds up in the bore 30 of the pump cylinder 12 thereby pushing the plunger 54 of the discharge valve 17 outwardly in the bore 83 thereby opening the discharge valve 17 and discharging an aliquot of gas—"the sample"—through the line I into the sample cylinder 90.

As the pump piston 13 reaches the end of its stroke, the actuator rod 8 contacts and actuates the button valve 11 opening the button valve 11 and allowing gas to flow through the port 11a, through the port 11b, through the line J, to the timer 80, resetting the timer 80. This resetting causes port 22b of the timer valve 22 to communicate with the port 22c through line M preventing gas from flowing from the port 22a to the port 22b and consequently to the button valve 11. The gas in the driver cylinder 5 and in the timer 80 are vented through the button valve ports 11a and 11c and through the lines G, F and K. This venting action is very rapid and allows the inlet gas from the gas source to flow again through the lines A and A2 into the bore 30 of the pump cylinder 12 forcing the piston 30, the piston rod 6 and the driver piston 4 back up into their ready position.

The instant that the pump piston 13 starts to move upwardly, the actuator rod 8 moves away from the button valve 11 allowing the button valve 11 to close. There is now no pressure on the driver piston 4 or on the resetting mechanism of the timer. High pressure has again been introduced into the bore 30 of the pump cylinder 12, into the line H, into the line B up to the regulator 26, and onto both sides of the relief valve 23. Reduced pressure from the regulator 26 is now in the line E and up to the port 22a of the timer 22.

At the expiration of the time set on the timer 80, the timer valve 22 operates so that port 22a is in communication with port 22b through line L allowing reduced pressure from the regulator 26 to flow through line E and through line F up to the inlet port 11a of the button valve 11. Simultaneously the gas flows through the line G to the driver cylinder 5 starting another cycle. This repeated operation continues at the frequency set on the timer 80 for the duration of the sampling period, which may be several days or several weeks. The sampling time may vary according to the desires of the user.

By supplying operating gas to the regulator 26 separately, the sampler 10 may be used to sample liquids. To sample liquids, the relief valve 23 is omitted. For sampling low pressure gases whose pressure is so low that they are incapable of forcing the return of the driver piston 4, the piston rod 6 and the pump piston 13, a return spring can be installed under the driver piston 4 in the driver cylinder 5 to force the return.

The high efficiency of the sampler 10 is obtained by the unique construction of the pump 64. The O-ring 38 is located on the pump piston 13 in such a manner that the dead volume is held to a minimum. Similarly, the volumes of the inlet valve 19, the discharge valve 17, and the right angle gas channels 78 and 79 are designed to be minimal. Also inlet valve 19 is designed to occupy a large part of the volume of the gas channel 78. This design insures that the volume of the sample will be accurate.

Accordingly, the sampler according to the present invention is well suited and adapted to obtain the objects and ends and has the advantages and features mentioned as well as other inherent therein. While a presently preferred embodiment of the invention has been given for the purpose of disclosure, changes in the details and arrangement of parts, in the apparatus may be made which are in the spirit of the invention as defined by the scope of the appended claims.

What is claimed is:

1. A sampler for sampling gas from a gas source and introducing the sample into a sample container, the sampler powered by the gas being sampled and comprising a pump means for pumping a sample of the gas from the source to the sample container, a timer connected to the pump for intervally activating the pump, a pressure regulator connected between the pump and the timer for regulating the pressure of the gas from the pump to the timer, a valve connected between the timer and the pump for resetting the timer.

2. A sampler for sampling gas from a gas source and introducing the sample into a sample container, the sampler powered by the gas being sampled and comprising a pump for pumping a sample from the source into the sample container, a timer connected to the pump for intervally activating the pump and initiating a sampling cycle, a pressure regulator connected between the pump and the timer and connected to the source for regulating the pressure of the gas to the timer for operating the timer, a valve connected to the timer and operable by a mechanical means connected to the pump for resetting the timer upon completion of a sampling cycle.

3. The sampler of claim 2 wherein the pump includes an inlet tube in communication with the gas source, an inlet valve for opening and closing off the inlet tube, a pump cylinder having a top and a bottom and in communication with the inlet tube for receiving the gas flowing through the inlet tube from the gas source, an outlet tube in communication with the pump cylinder and the sample container through which the sample flows from the pump cylinder to the sample container, an outlet valve mounted in the outlet tube for opening and closing off the outlet tube, a purge valve mounted in the bottom of the pump cylinder for purging the pump cylinder at the beginning of each sampling cycle, a pump piston movably mounted in the pump cylinder and operated by pressurized gas from the timer for moving the sample from the pump cylinder, through the outlet valve, through the outlet tube and into the sample container.

4. An automatic sampler for sampling fluid from a fluid source and introducing the sample into a sample container, the sampler comprising a pump for pumping a sample of the fluid from the fluid source into the sample container, the pump including an inlet tube in communication with the fluid source, a pump cylinder having a top and a bottom in communication with the inlet tube for receiving the fluid flowing through the inlet tube from the fluid source, an inlet channel extending from the inlet tube to the pump cylinder, an inlet valve for opening and closing off the inlet tube, the valve comprising a plunger movably mounted in the inlet channel, an inlet O-ring mounted in the inlet tube, a spring for urging the plunger into contact with the inlet O-ring, the plunger yieldably mounted so that pressurized fluid from the fluid source will push the plunger back into the inlet channel against the spring permitting fluid to flow through the inlet channel and into the pump cylinder, the plunger formed so that it restricts the volume of fluid in the inlet channel, an outlet tube in communication with the pump cylinder and the sample container through which the sample flows from the pump cylinder to the sample container, an outlet channel extending from the pump cylinder to the outlet tube, an outlet valve mounted in the outlet tube for opening and closing off the outlet tube at the point at which the outlet tube communicates with the outlet channel, the outlet valve comprising an outlet O-ring mounted in the outlet tube and a spring-biased plunger movably mounted in the outlet tube so that the plunger is yieldably urged into the outlet O-ring by the spring thereby closing off the outlet tube and preventing the flow of fluid from the outlet channel into the outlet tube, a purge valve mounted in the bottom of the pump cylinder for purging the pump cylinder at the beginning of each sampling cycle, the purge valve having a purge valve O-ring mounted therein, a pump piston movably mounted in the pump cylinder for moving the sample from the pump cylinder, through the outlet channel and the outlet valve, through the outlet tube and into the sample container, a stinger mounted to and projecting from the pump piston so that movement of the piston moves the stinger into contact with the purge valve O-ring thereby closing the purge valve, a timer connected to the pump for intervally activating the pump and initiating a sampling cycle a pressure regulator connected between the pump and the timer and connected to the fluid source for regulating the pressure of the fluid flowing to the timer for operating the timer, a valve connected to the timer and operable by a mechanical means connected to the pump for resetting the timer upon completion of each sampling cycle, and the pressurized fluid flowing from the timer during a sampling cycle to the pump to force the pump piston downward in the pump cylinder.

5. A sampler for sampling liquid from a liquid source and introducing the sample into a sample container comprising a pump means for pumping a sample of the liquid from the liquid source to the sample container, a timer connected to the pump for intervally activating the pump, a gas source connected to the timer, a pressure regulator connected between the gas source and the timer for regulating the pressure of the gas from the gas source to the timer, and a valve connected between the timer and the pump for resetting the timer.

6. A sampler for sampling liquid from a liquid source and introducing the sample into a sample container, the sampler comprising a pump for pumping a sample from the liquid source into the sample container, a timer connected to the pump for intervally activating the pump and initiating a sampling cycle, a gas source connected to the timer, a gas-operated pressure regulator connected between the gas source and the timer for regulating the pressure of the gas from the gas source to the timer, and a valve connected to the timer and operable by a mechanical means connected to the pump for resetting the timer upon completion of a sampling cycle.

7. The sampler of claim 6 wherein the pump includes an inlet tube in communication with the liquid source, an inlet valve for opening and closing off the inlet tube, a pump cylinder having a top and a bottom and in communication with the inlet tube for receiving the liquid flowing through the inlet tube from the liquid source, an outlet tube in communication with the pump cylinder and the sample container through which the sample flows from the pump cylinder to the sample container, an outlet valve mounted in the outlet tube for opening and closing off the outlet tube, a purge valve mounted in the bottom of the pump cylinder for purging the pump cylinder at the beginning of each sampling cycle, a pump piston movably mounted in the pump cylinder and operated by pressurized gas from the gas source for moving the sample from the pump cylinder, through the outlet valve, through the outlet tube and into the sample container.

* * * * *